(12) United States Patent
Tian et al.

(10) Patent No.: US 11,723,873 B2
(45) Date of Patent: Aug. 15, 2023

(54) ORAL DOSAGE FORM OF TICAGRELOR AND PREPARATION METHOD THEREOF

(71) Applicant: Elite Pharmaceutical Solution Inc., Princeton, NJ (US)

(72) Inventors: Wu Tian, Princeton, NJ (US); Yan Wang, Princeton, NJ (US); Henry Tian, Princeton, NJ (US)

(73) Assignee: Elite Pharmaceutical Solution Inc., Princeton, NJ (US)

( * ) Notice: Subject to any disclaimer, the term of this patent is extended or adjusted under 35 U.S.C. 154(b) by 0 days.

(21) Appl. No.: 17/356,120

(22) Filed: Jun. 23, 2021

(65) Prior Publication Data
US 2022/0409545 A1    Dec. 29, 2022

(51) Int. Cl.
 *A61K 9/20*    (2006.01)
 *A61K 31/519*    (2006.01)
 *A61K 9/28*    (2006.01)

(52) U.S. Cl.
CPC .......... *A61K 9/2086* (2013.01); *A61K 9/2018* (2013.01); *A61K 9/2027* (2013.01); *A61K 9/2031* (2013.01); *A61K 9/2054* (2013.01); *A61K 9/2886* (2013.01); *A61K 31/519* (2013.01)

(58) Field of Classification Search
CPC .. A61K 31/519; A61K 9/2086; A61K 9/2886; A61K 9/2031
See application file for complete search history.

(56) References Cited

U.S. PATENT DOCUMENTS

2007/0259033 A1*  11/2007  Cruz .................... A61K 31/165
424/452

FOREIGN PATENT DOCUMENTS

CN    111450072 A  *  7/2020  .......... A61K 31/519

* cited by examiner

*Primary Examiner* — Lakshmi S Channavajjala
(74) *Attorney, Agent, or Firm* — Pattao, LLC; Junjie Feng (57) ABSTRACT

An oral dosage form of ticagrelor includes a core and a semi-permeable membrane coating the core. The core comprises a first drug layer and a push layer. The first drug layer contains ticagrelor that is sufficient to deliver an effective amount of the drug over an intended delivery time. The push layer comprises a swelling agent and an osmogen agent. The semi-permeable membrane has at least one passageway formed therethrough, positionally configured to face the first drug layer, but not to face the push layer, of the core, and functionally configured to allow the ticagrelor to realize an extended release out of the core upon contacting an aqueous environment. The dosage form optionally further includes a second ticagrelor-containing drug layer coating the semi-permeable membrane, thereby providing a starting effective dose upon administration. The dosage form can realize once-a-day administration of ticagrelor of patients in need thereof.

19 Claims, 5 Drawing Sheets

ORAL DOSAGE FORM OF TICAGRELOR AND PREPARATION METHOD THEREOF

TECHNICAL FIELD

The present disclosure relates generally to pharmaceutical compositions of treating or preventing thrombosis, and more specifically to an oral dosage form adapted to deliver the antithrombotic agent ticagrelor and a preparation method thereof.

BACKGROUND

As an antiplatelet or antithrombotic medication, ticagrelor is commonly used for preventing or treating stroke, heart attack and other events in people with acute coronary syndrome (ACS) or a history of myocardial infarction (MI), etc. Ticagrelor is currently sold in the market under the brand name Brilinta among others.

Ticagrelor has an empirical formula of $C_{23}H_{28}F_2N_6O_4S$ and a molecular weight of 522.57 Da, and is also known by its chemical name (1S,2S,3R,5S)-3-[7-{[(1R,2S)-2-(3,4-difluorophenyl)cyclopropyl] amino}-5-(propylthio)-3H-[1,2,3]-triazolo[4,5-d]pyrimidin-3-yl]-5-(2-hydroxyethoxy)cyclopentane-1,2-diol. The chemical structure of ticagrelor is as follows:

At room temperature, ticagrelor is a crystalline powder with an aqueous solubility of approximately 10 μg/mL. With the current design of product in the market, ticagrelor has an absorption profile such that after administration, the absorption of ticagrelor occurs with a median time ($T_{max}$) to reach the peak plasma concentration ($C_{max}$) of 1.5 hours, with $t_{max}$ ranging from approximately 1.0 hours to approximately 4.0 hours, and the formation of the major circulating metabolite AR-C124910XX from ticagrelor occurs with a median time ($T_{max}$) of approximately 2.5 hours and a range of approximately 1.5 hours to approximately 5.0 hours. As such, it typically requires a patient to take a tablet every 12 hours or more often thereby bringing issues of inconvenience or potential noncompliance.

The present disclosure generally relates to methods of for preventing or treating stroke, heart attack and other events in people with acute coronary syndrome (ACS) or a history of myocardial infarction (MI). In one aspect, the present disclosure relates to methods for reducing the rate of cardiovascular death, myocardial infarction, or stroke in a patient with a history of myocardial infarction, comprising administering once daily to the patient a pharmaceutical composition comprising 120-180 mg ticagrelor and a pharmaceutically acceptable carrier. In another aspect, the present disclosure relates to methods for reducing the rate of cardiovascular death, myocardial infarction, or stroke in a patient with acute coronary syndrome, comprising administering once daily to the patient a pharmaceutical composition comprising 60-180 mg ticagrelor and a pharmaceutically acceptable carrier.

SUMMARY OF THE INVENTION

In order to address the above mentioned issues associated with current formulation or dosage forms of ticagrelor, the present disclosure provides a dosage delivery form adapted to deliver ticagrelor (i.e. dosage form of ticagrelor) to a subject in need, such as people with stroke, heart attack acute coronary syndrome (ACS), or a history of myocardial infarction (MI).

The dosage form of ticagrelor comprises a core and a semi-permeable membrane coating an outside of the core. The core comprises a first drug layer and a push layer which are substantially stacked over one another. The first drug layer comprises the active medication ticagrelor in an amount sufficient to deliver an effective amount thereof over an intended delivery time, and the push layer comprises a swelling agent and an osmogen agent.

The semi-permeable membrane is provided with at least one passageway, which is formed through the semi-permeable membrane. The at least one passageway is positionally configured to face the first drug layer, but not to face the push layer, of the core, and is functionally configured to allow the ticagrelor in the first drug layer to release out of the core therethrough when the dosage delivery form is in an aqueous environment.

Herein, according to preferred embodiments of the dosage form, the intended delivery time of ticagrelor is 24 hours, thereby realizing a once-a-day administration of ticagrelor for subjects in need thereof.

Depending on different design and configuration, the dosage form of ticagrelor can realize that less than 80%, and preferably less than 70% of the ticagrelor is released at approximately 12 hours after dissolution in water.

According to certain embodiments of the dosage form of ticagrelor, less than 90% of the ticagrelor is released at approximately 16 hours after dissolution in water.

According to certain embodiments of the dosage form of ticagrelor, a variation of a release rate of the ticagrelor (i.e. variation in ticagrelor release rate) is less than approximately 20% at approximately 8-12 hours. As used herein, the term "variation of a release rate", "release rate variation", or alike, is calculated as an absolute value of: (current hour release rate−last hour release rate)/last hour release rate*100%.

According to certain embodiments of the dosage form of ticagrelor, the amount of the ticagrelor in the first drug layer is from about 50 mg to about 200 mg, and preferably about 60-180 mg.

According to certain embodiments, the dosage form of ticagrelor further includes a second drug layer coating an outside of the semi-permeable membrane, and the second drug layer also comprises the ticagrelor. As such, compared with those embodiments without the ticagrelor-containing second drug layer, these embodiments of the dosage form substantially can provide a better starting effective dosage of ticagrelor.

In these second drug layer-containing embodiments of the dosage form, the intended delivery time of ticagrelor is preferably 24 hours, and accordingly, a sum of the amount of the ticagrelor in the first drug layer and an amount of the ticagrelor in the second drug layer is from about 50 mg to about 200 mg, and preferably about 60-180 mg. Herein, optionally, the amount of the ticagrelor in the first drug layer and the amount of the ticagrelor in the second drug layer can be between approximately 30-90 mg and between approximately 30-90 mg, respectively.

Further according to some preferred embodiments, more than 15% of the ticagrelor is released at approximately 1 hour after dissolution in water.

In these second drug layer-containing embodiments, the dosage form can further include a cosmetic coating layer coating an outside of the second drug layer.

In any of the embodiments of the dosage delivery form as described above, the swelling agent in the push layer may comprise polyethylene oxide having an amount of about 40% to about 80% in the push layer by weight.

Optionally, the swelling agent may comprise at least one of Polyethylene Oxide WSR coagulate, Polyethylene Oxide WSR 301, or Polyethylene Oxide WSR 303. As used herein, and throughout other part of the disclosure as well, Polyethylene Oxide (PEO) WSR is to be interpreted according to the regular meaning as commonly understood by people of ordinary skills in the field, and is specifically referred to as a water soluble resin (i.e. WSR). Polyethylene Oxide WSR 301 (i.e. "PEO WSR 301", or "PEO 301") has a molecular weight of approximately 4,000,000 g/mol, Polyethylene Oxide WSR coagulant (i.e. "PEO WSR coagulant") has a molecular weight of approximately 5,000,000 g/mol, and Polyethylene Oxide WSR 303 (i.e. "PEO WSR 303", or "PEO 303") has a molecular weight of approximately 7,000,000 g/mol.

In any of the embodiments of the dosage delivery form as described above, the osmogen agent in the push layer may comprise at least one soluble inorganic salt, such as magnesium chloride, magnesium sulfate, lithium chloride, sodium chloride, potassium chloride, lithium hydrogen phosphate, sodium hydrogen phosphate, potassium hydrogen phosphate, lithium hydrogen phosphate, sodium hydrogen phosphate, potassium dihydrogen phosphate, or soluble salt of organic acid such as sodium acetate, potassium acetate, magnesium succinate, sodium benzoate, sodium citrate, and sodium ascorbate. Herein, preferably, the osmogen agent in the push layer comprises sodium chloride having an amount of about 10% to about 40% in the push layer by weight.

Alternatively, the osmogen agent in the push layer may comprise at least one non-ionic organic compound, such as arabinose, ribose, xylose, glucose, fructose, mannose, galactose, sucrose, maltose, lactose, and raffinose.

According to certain embodiments of the dosage form, the osmogen agent in the push layer may comprise a mix of at least one soluble inorganic salt and at least one non-ionic organic compound.

In any of the embodiments of the dosage delivery form as described above, the semi-permeable membrane can comprise at least one membrane polymer (i.e. "membrane polymer", "controlling polymer", or a like), which can have a relative amount of approximately 60% to 100% of the semi-permeable membrane film by weight. Examples of the membrane polymer can include cellulose esters, cellulose diesters, cellulose triesters, cellulose ethers, cellulose acetate phthalate, cellulose acetate, cellulose diacetate, cellulose triacetate, cellulose acetate propionate, and cellulose acetate butyrate, etc. Other suitable polymers are described in U.S. Pat. Nos. 3,845,770, 3,916,899, 4,008,719, 4,036,228 and 4,11210 which are incorporated herein by reference.

Preferably, the at least one membrane polymer in the semi-permeable membrane may comprise at least one of the following: cellulose acetate, cellulose diacetate, cellulose triacetate, polyurethane, polyamide, sulfonated polystyrene, cellulose acetate valerate, or cellulose acetate succinate.

More preferably, the at least one membrane polymer in the semi-permeable membrane may comprise cellulose acetate having an amount of about 80% to about 100% in the semi-permeable membrane wall by weight. Herein, the cellulose acetate may be selected from CA-320S, CA-398-3, CA398-6, CA 398-10, CA 398-30, CA398-60S.

According to certain embodiments of the dosage form, the semi-permeable membrane further comprises at least one plasticizing agent having a relative amount of approximately 0.1-40% of the semi-permeable membrane by weight.

Herein, the at least one plasticizing agent may comprise a polyglycol, such as a polyalkylene glycol (PAG) or a polyethylene glycol (PEG) having a molecular weight of 300-8000.

Preferably, the at least one plasticizing agent comprises a polyethylene glycol (PEG), selected from PEG 6000 or PEG 8000.

According to some embodiments of the oral dosage form, the at least one passageway on the semi-permeable membrane may be mechanically or optically created.

As used herein the term "passageway" may include an aperture, orifice, bore, hole, weakened area or an erodible element such as a gelatin plug that erodes to form an osmotic passageway for the release of the active drug from the core of the dosage form. A detailed description of the passageway can be found in U.S. Pat. Nos. such as U.S. Pat. Nos. 3,845,770, 3,916,899, 4,034,758, 4,063,064, 4,077,407, 4,088,864, 4,783,337, and 5,071,607 (the disclosures of which are hereby incorporate by reference).

In certain embodiments, the passageway is formed by laser drilling. In preferred embodiments, the dosage form contains one passageway on the drug side of each tablet in order provide the desired pharmacokinetic parameters of the formulation.

In preferred embodiments, the orifice passageway should be within ±5 mm of the middle of one side of the tablet, diameter of orifice should be between 0.20 to 2.00 mm, depth of orifice should be between 0.10 to 2.50 mm.

In the core in any of the embodiments of the dosage delivery form as described above, the first drug layer may, in addition to the active medication agent ticagrelor, further comprise other pharmaceutically acceptable carriers or excipients, such as one or more suspending agents, osmogen agents, surfactants, binding agents, lubricants, and coloring agents.

Herein, the suspending agent in the first drug layer can comprise polyethylene oxide in an amount of about 40% to about 80% in the first drug layer by weight.

The binding agent in the first drug layer can be selected from hydroxypropyl methylcellulose (HPMC), hydroxylpropyl cellulose (HPC), hydroxyethyl cellulose (HEC), poly (ethylene) oxide (PEO), polyvinyl alcohol (PVA), povidone (PVP), and co-povidone. Mixtures of the above-mentioned binding agents may also be used. The one or more binding agents can be present in an amount of about 2% to about 15% in the first drug layer by weight. Herein, the preferred binding agents are water soluble such as polyvinyl pyrrolidone having a weight average molecular weight of 25,000 to 3,000,000.

Similar to the osmogen agent in the push layer, the osmogen agent in the first drug layer can comprise either or both of a soluble inorganic salt and a non-ionic organic compound. Examples can be found in the osmogen agent in the push layer as described above.

Herein, the surfactants (i.e. absorption enhancers) in the first drug layer can be selected from sodium lauryl sulfate, sodium taurocholate, and polysorbate 80, chelating agents such as citric acid, phytic acid, ethylenediamine tetraacetic acid (EDTA), and ethylene glycol-big (B-aminoethyl ether-N,N,N,N-tetraacetic acid (EGTA)). The core comprises approximately 0 to about 20% of the absorption enhancer based on the total weight of the core and most preferably about 2% to about 10% of the total weight of the core.

Herein, the lubricant in the first drug layer can be selected from magnesium stearate, stearate acid, etc., and can be present in an amount of about 0.1% to about 2% in the first drug layer by weight.

Further in the core in any of the embodiments of the dosage delivery form as described above, the push layer may, in addition to the at least one swelling agent and the at least one osmogen agent, further include other pharmaceutically acceptable carriers or excipients, such as one or more binding agents, lubricants, and coloring agents.

Herein, the binding agent in the push layer can be selected from hydroxypropyl methylcellulose (HPMC), hydroxylpropyl cellulose (HPC), hydroxyethyl cellulose (HEC), poly(ethylene) oxide (PEO), polyvinyl alcohol (PVA), povidone (PVP), and co-povidone. Mixtures of the above-mentioned binding agents may also be used. The binding agent can be present in an amount of about 2% to about 15% in the first drug layer by weight. The preferred binding agents are water soluble such as polyvinyl pyrrolidone having a weight average molecular weight of 25,000 to 3,000,000.

The lubricant in the push layer of the first drug layer can be selected from magnesium stearate, stearate acid, etc., and can be present in an amount of about 0.1% to about 2% in the first drug layer by weight.

DETAILED DESCRIPTION

In the following, with reference to the above-mentioned drawings of various embodiments disclosed herein, the technical solutions of the various embodiments of the disclosure will be described in a clear and fully understandable way. It is noted that the described embodiments shall represent merely a portion, but not all, of the embodiments of the disclosure. Based on the described embodiments of the disclosure, those ordinarily skilled in the art can obtain other embodiment(s), which shall come within the scope sought for protection by the disclosure.

In general, the present disclosure provides oral dosage forms of ticagrelor, which can be used for preventing or treating stroke, heart attack and other events in people with acute coronary syndrome (ACS) or a history of myocardial infarction (MI) in a subject (i.e. "patients in need" hereinafter).

To be more specific, the present disclosure provides a controlled-release dosage form of ticagrelor, which can be suitable for once-a-day administration to patients in need. The dosage form comprises an effective amount of the drug for preventing or treating stroke, heart attack for up to about 24 hours.

Figure 1A:
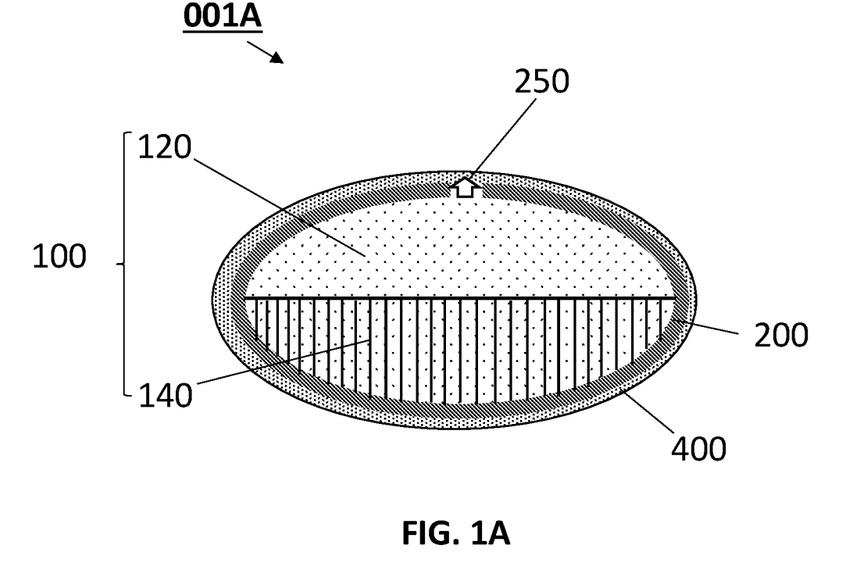
FIGS. 1A and 1B respectively illustrate the schematic structure of the oral dosage form of ticagrelor according to two different embodiments of the present disclosure.
Figure 1B:
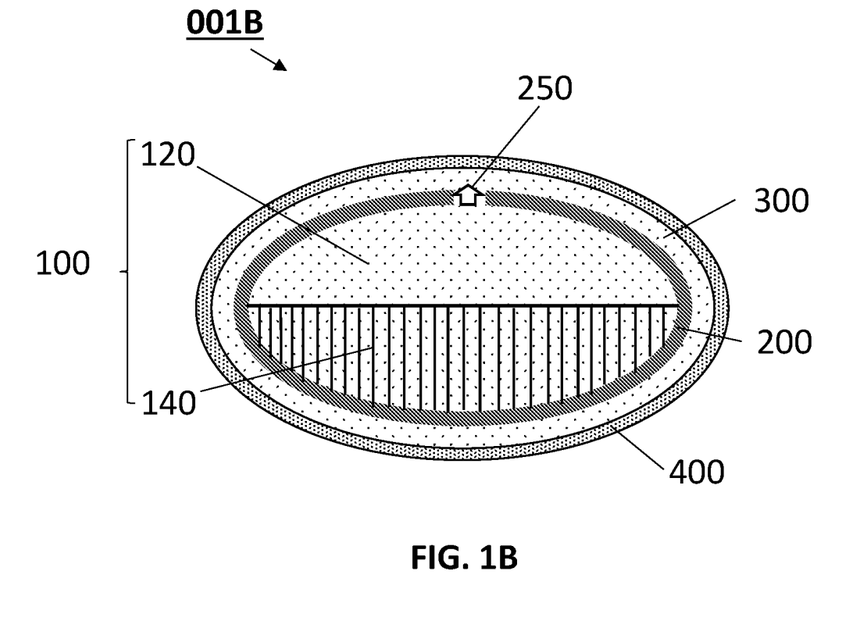
Figure 2:
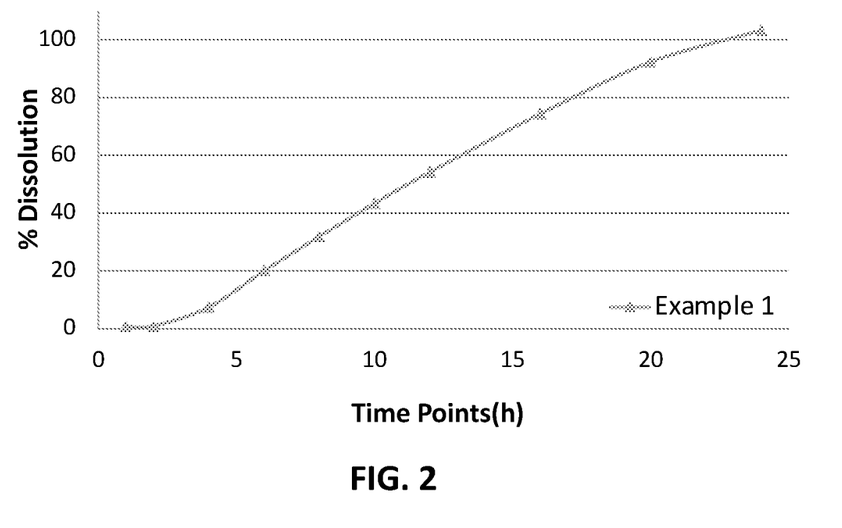
FIG. 2 is a graph showing the dissolution profile of 180 mg Ticagrelor ER Tablets of Example 1 of the present disclosure.
Figure 3:
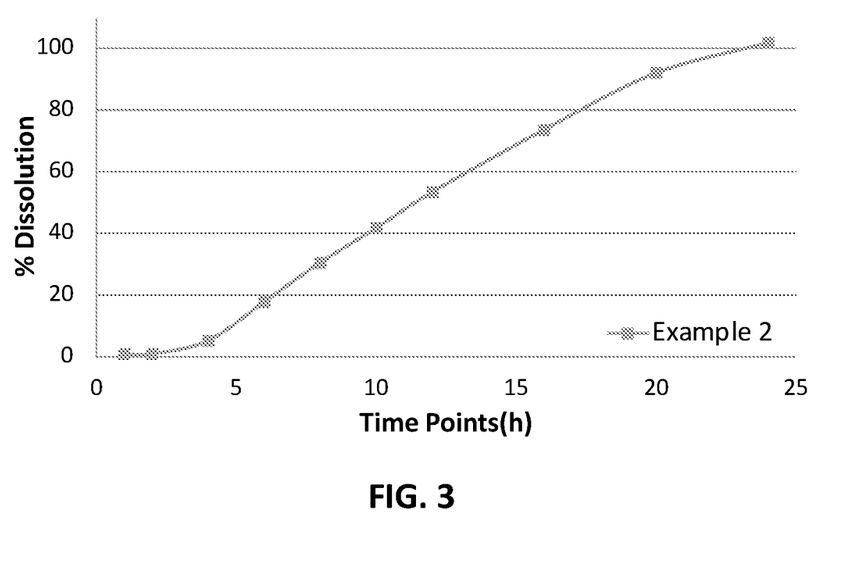
FIG. 3 is a graph showing the dissolution profile of 120 mg Ticagrelor ER Tablets of Example 2 of the present disclosure.
Figure 4:
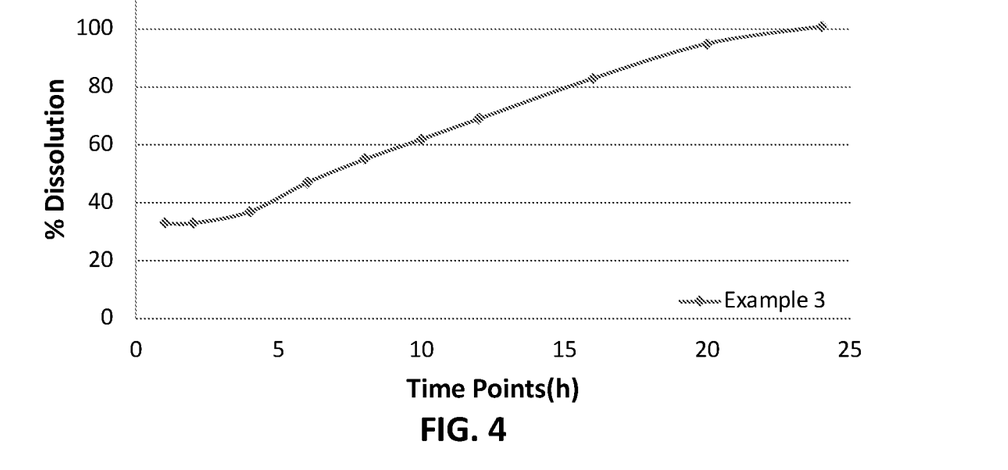
FIG. 4 is a graph showing the dissolution profile of 180 mg Ticagrelor ER Tablets of Example 3 of the present disclosure.
Figure 5:
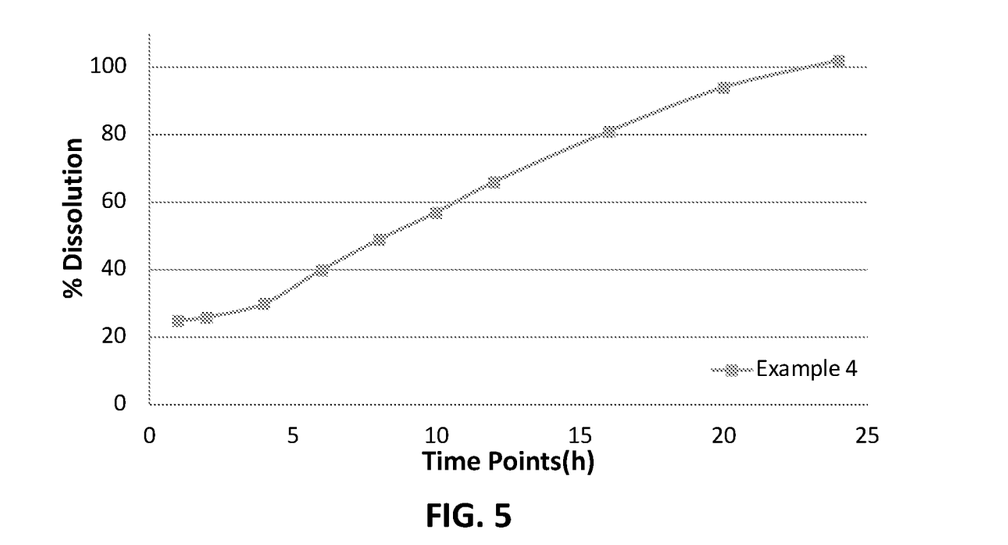
FIG. 5 is a graph showing the dissolution profile of 180 mg Ticagrelor ER Tablets of Example 4 of the present disclosure.
Figure 6:
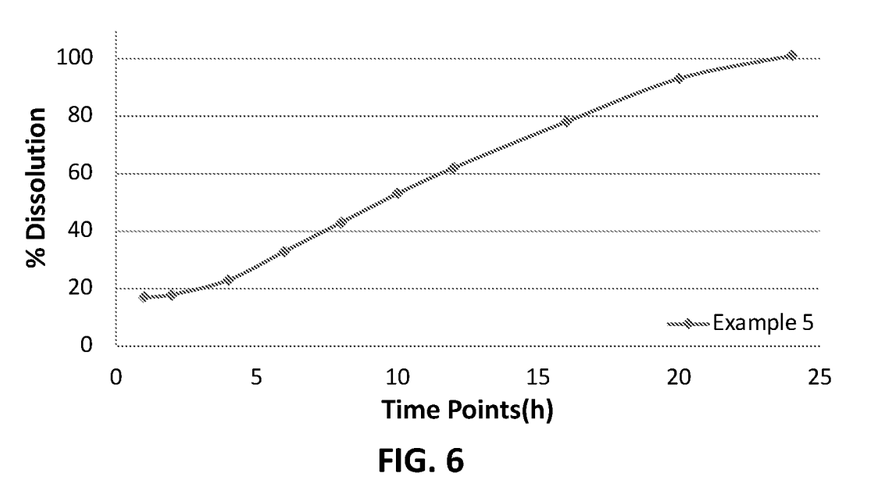
FIG. 6 is a graph showing the dissolution profile of 180 mg Ticagrelor ER Tablets of Example 5 of the present disclosure.
Figure 7:
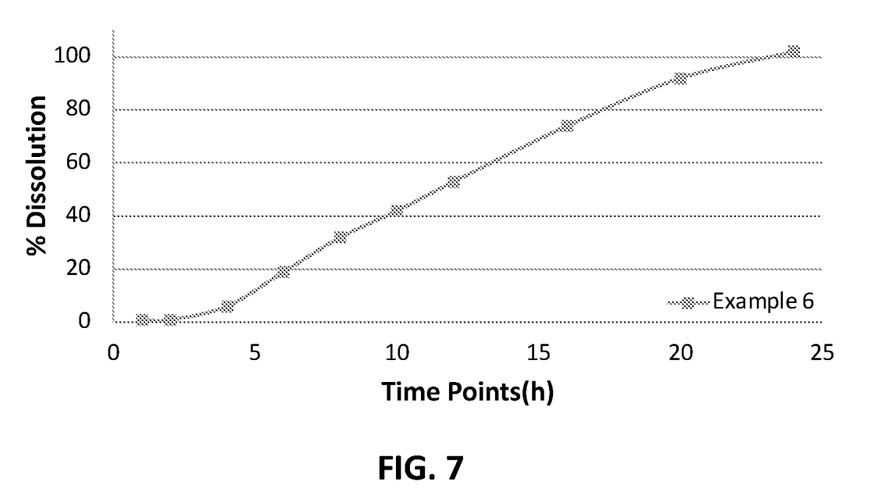
FIG. 7 is a graph showing the dissolution profile of 60 mg Ticagrelor ER Tablets of Example 6 of the present disclosure.
Figure 8:
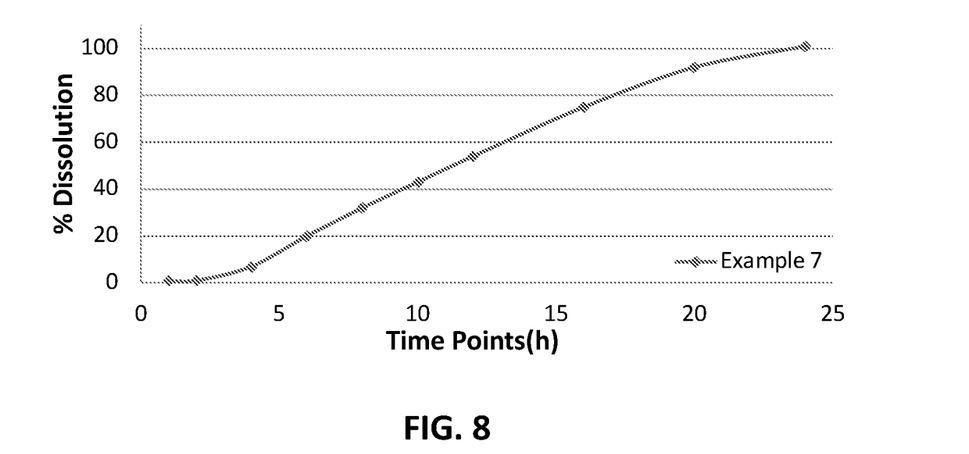
FIG. 8 is a graph showing the dissolution profile of 90 mg Ticagrelor ER Tablets of Example 7 of the present disclosure.
Figure 9:
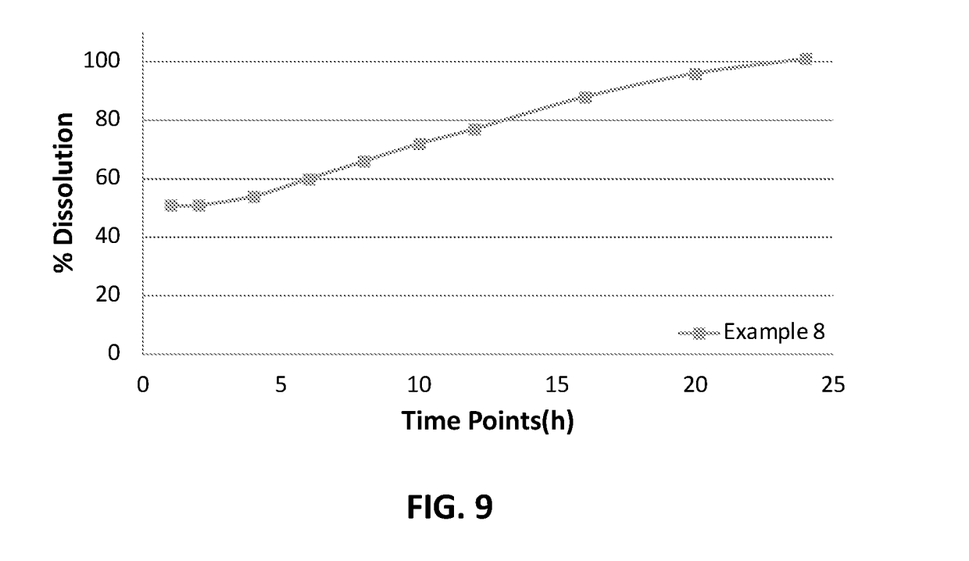
FIG. 9 is a graph showing the dissolution profile of 180 mg Ticagrelor ER Tablets of Example 8 of the present disclosure.

FIG. 1A and FIG. 1B illustrate a schematic structure of the oral dosage form of ticagrelor according to two embodiments of the disclosure.

As shown in FIG. 1A, the first embodiment of the oral dosage form of ticagrelor 001A substantially comprises a core 100 and a semi-permeable membrane 200 that securely surrounds or coats an outside of the core 100. The core 100 is substantially in a bilayer structure, including a drug layer 120 (called "first drug layer 120" to differentiate with an additional drug layer, called "second drug layer 300", in the second embodiment illustrated in FIG. 1B) and a push layer 140 that are stacked over one another.

The first drug layer 120 comprises the active agent (i.e. ticagrelor) in an amount sufficient to deliver an effective amount thereof over an intended delivery time (e.g. 24 hours) for the dosage form. The push layer comprises at least a swelling agent and an osmogen agent.

The semi-permeable membrane 200 is provided with at least one passageway 250 that is formed through the semi-permeable membrane 200 to thereby connect the core 100 with an external environment (i.e. the environment that is outside of the semi-permeable membrane 200; not shown in FIG. 1A). Specifically, the at least one passageway 250 is configured to have a relative position on the semi-permeable membrane 200 such that the at least one passageway 250 faces the first drug layer 120, but does not face the push layer 140, of the core 100. As illustrated in FIG. 1A, the at least one passageway 250 is arranged at a position that is substantially over a top surface of the first drug layer 120 that is opposing to the push layer 140. The at least one passageway 250 is configured to allow the ticagrelor in the first drug layer 120 to release out of the core therethrough when the dosage delivery form is in an aqueous environment, such as in the gastrointestinal (i.e. GI) tract of the subject taking the oral dosage form of ticagrelor.

Because of the above structure and compositions for each layer of the above embodiment of the oral dosage form of ticagrelor, a controlled or extended release of ticagrelor after oral administration can be realized. More details can be found in several examples, including Example 1, 2, 6 and 7, below.

It is noted that optionally, this first embodiment of the dosage delivery form may further include a cosmetic coating layer 400 which coats an outside of the semi-permeable membrane 200, which is also illustrated in FIG. 1A.

A slightly different embodiment of the above described oral dosage form of ticagrelor is further provided in FIG. 1B.

In this embodiment, all of the layers, their main compositions, and configurations in the first embodiment illustrated in FIG. 1A, including the first drug layer 120 and the push layer 140 in the core 100, and the semi-permeable membrane 200 provided with at least one passageway 250, remain the same, yet as illustrated in FIG. 1B, this second embodiment of the oral dosage form of ticagrelor further comprises a second drug layer 300, which surrounds or coats an outside of the semi-permeable membrane 200. Same as the first drug layer 120, the second drug layer 300 also comprises the active agent ticagrelor, which ensures that the active ticagrelor can be released in sufficient amount early even after a short time period of administration.

Optionally, this second embodiment of the dosage delivery form may further include a cosmetic coating layer 400 which coats an outside of the second drug layer 300.

In some embodiments of the pharmaceutical composition, ticagrelor is only in the first drug layer 120 in an amount sufficient to deliver an effective amount thereof over the intended delivery time-24 hours.

In some embodiments of the pharmaceutical composition, ticagrelor is both in the first drug layer 120 in the core 100 in an amount sufficient to deliver an effective amount thereof over the intended delivery time-24 hours, and is also in the second drug layer 300 to deliver an effective amount in approximately 1 hour.

Each of the two portions of the drug can be further configured to have a dosage and/or a formulation optimized such that when the pharmaceutical composition is orally administered in the subject, the drug agent can have an early effective time and keep the effective drug concentration in human body for approximately 15-24 hours.

Herein, any part of drug agent can be configured to be in an immediate-release formulation or in a controlled release formulation according to an established PK/PD profile thereof.

Regarding the immediate-release formulation of the drug agent in the pharmaceutical composition, the oral dosage form of the drug agent can be provided as granules, spheroids, beads, pellets, particles (hereinafter collectively referred to as "multiparticulates") or existing in a coating layer. An amount of the multiparticulates which is effective to provide the desired dose of drug over time may be placed in a capsule or may be incorporated in any other suitable oral form.

An oral osmotic dosage delivery form adapted to deliver ticagrelor in 24 hours may comprise a bilayer tablet core, and the core is coated with a semipermeable membrane to thereby substantially generate an osmotic device allowing an extended release of the agent from the core through delivery orifices or delivery pores in the semipermeable membrane.

One layer in the bilayer tablet core is the drug layer including ticagrelor in an amount sufficient to deliver an effective amount thereof over the intended delivery time-24 hours, and one or more suspending agents, with or without one or more osmogen agents, with or without one or more binding agents, with or without one or more lubricants, and with or without a coloring agent.

Furthermore, wherein said suspending agent in the drug layer is polyethylene oxide, are selected from different grades of polyethylene oxide, said suspending agent being present in an amount of about 40% to about 80% in the drug layer by weight based upon the amount said ticagrelor amount. Herein, Polyethylene Oxide WSR N80 (i.e. "PEO WSR N80") that has a molecular weight of approximately 200,000 g/mol can be used as a suspending agent in the drug layer.

Furthermore, wherein said binding agent in the drug layer can be selected from hydroxypropyl methylcellulose (HPMC), hydroxyl-propyl cellulose (HPC), hydroxyethyl cellulose (HEC), poly(ethylene) oxide (PEO), polyvinyl alcohol (PVA), povidone (PVP), and co-povidone. Mixtures of the above-mentioned binding agents may also be used. The said binding agent being present in an amount of about 2% to about 15% in the drug layer by weight based upon the amount said ticagrelor amount. The preferred binding agents are water soluble such as polyvinyl pyrrolidone having a weight average molecular weight of 25,000 to 3,000,000.

Furthermore, wherein said osmogen agent in the drug layer could be selected from such as soluble salt of inorganic salt such as magnesium chloride, magnesium sulfate, lithium chloride, sodium chloride, potassium chloride, lithium hydrogen phosphate, sodium hydrogen phosphate, potassium hydrogen phosphate, lithium hydrogen phosphate, sodium hydrogen phosphate, potassium dihydrogen phosphate, or soluble salt of organic acid such as sodium acetate, potassium acetate, magnesium succinate, sodium benzoate, sodium citrate, sodium ascorbate, non-ionic organic compound such as: arabinose, ribose, xylose, glucose, fructose, mannose, galactose, sucrose, maltose, lactose, raffinose.

Furthermore, the surfactants in the drug layer could be selected from sodium lauryl sulfate, sodium taurocholate and polysorbate 80, chelating agents such as citric acid, phytic acid, ethylenediamine tetraacetic acid (EDTA) and ethylene glycol-big (B-aminoethyl ether-N,N,N,N-tetraacetic acid (EGTA)). The core comprises approximately 0 to about 20% of the absorption enhancer based on the total weight of the core and most preferably about 2% to about 10% of the total weight of the core. Other commonly known excipients may also be included into the drug layer such as lubricants, pigments or dyes.

Furthermore, wherein said lubricant in the drug layer could be selected from magnesium stearate, stearate acid, etc. The said lubricant being present in an amount of about 0.1% to about 3% in the drug layer by weight based upon the amount said ticagrelor amount.

Furthermore, wherein said swelling agent or pushing agent in the push layer is Polyethylene Oxide, are selected from different grades of Polyethylene Oxide WSR coagulate, Polyethylene Oxide WSR 301 or Polyethylene Oxide WSR 303, said pushing agent being present in an amount of about 40% to about 80% in the push layer by weight based upon the amount said ticagrelor amount.

Furthermore, wherein said binding agent in the push layer can be selected from hydroxypropyl methylcellulose (HPMC), hydroxyl-propyl cellulose (HPC), hydroxyethyl cellulose (HEC), poly(ethylene) oxide (PEO), polyvinyl alcohol (PVA), povidone (PVP), and co-povidone. Mixtures of the above-mentioned binding agents may also be used. The said binding agent being present in an amount of about 2% to about 15% in the drug layer by weight based upon the amount said ticagrelor amount. The preferred binding agents are water soluble such as polyvinyl pyrrolidone having a weight average molecular weight of 25,000 to 3,000,000.

Furthermore, wherein said osmogen agent in the push layer are selected from such as soluble salt of inorganic salt such as magnesium chloride, magnesium sulfate, lithium chloride, sodium chloride, potassium chloride, lithium hydrogen phosphate, sodium hydrogen phosphate, potassium hydrogen phosphate, lithium hydrogen phosphate, sodium hydrogen phosphate, potassium dihydrogen phosphate, or soluble salt of organic acid such as sodium acetate, potassium acetate, magnesium succinate, sodium benzoate, sodium citrate, sodium ascorbate, non-ionic organic compound such as: arabinose, ribose, xylose, glucose, fructose, mannose, galactose, sucrose, maltose, lactose, raffinose.

Furthermore, osmogen agent in the push layer are sodium chloride, said osmogen agent being present in an amount of about 10% to about 40% in the push layer by weight based upon the amount said ticagrelor amount.

Furthermore, the other commonly known excipients may also be included into the push layer such as lubricants, pigments or dyes.

Furthermore, wherein said lubricant in the drug layer could be selected from magnesium stearate, stearate acid, xx. The said lubricant being present in an amount of about 0.1% to about 3% in the drug layer by weight based upon the amount said ticagrelor amount.

Preferably, the semipermeable membrane described above includes semi-permeable polymer and soluble excipients (i.e. pore-forming agents). The semi-permeable polymer that are useful in forming the membrane are cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate, and cellulose acetate butyrate. The most preferred membrane material is cellulose acetate CA-398-10 comprising an acetyl content of 39.3%-40.3%, commercially available for Eastman Fine Chemicals.

In an alternative embodiment the membrane can be formed from the above-described polymers and a pore-forming agent (i.e. flux enhancing agent). The flux enhancing agent, or the flux enhancer, increases the volume of fluid (e.g. water and biological fluid) penetrating into the core to make the push layer to swell and enable drug layer to liquidize so the push layer can push the drug layer through the orifice to the GI system. The flux enhancing agent can be a water-soluble material or an enteric material. Some examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methylcellulose, hydroxypropy methylcellulose phthalate, cellulose acetate phthalate, polyvinyl alcohols, methacrylic acid copolymers and mixtures thereof. The preferred flux enhancer is PEG 6000 and PEG 8000 i.e. The flux enhancing agent comprises approximately 0 to about 40% of the total weight of the coating, most preferably about 2% to about 20% of the total weight of the coating. The flux enhancer may also be a drug that is water soluble or its pharmaceutically acceptable salts or a drug that is soluble under intestinal conditions.

More preferably, the membrane may also be formed with commonly known excipients such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer, amounts of from 0 to about 25%.

Generally, the membrane coating (i.e. semi-permeable membrane) around the core comprises from about 3% to about 20%, preferably about 7% to about 13%, based on the total weight of the core and coating.

According to some embodiments of the oral dosage form of the pharmaceutical composition, at least one passageway is mechanically or optically created in the middle of membrane coated tablets.

As used herein the term "passageway" can include, and is interchangeable with, the following terms including aperture, orifice, bore, hole, weakened area, or an erodible element such as a gelatin plug that erodes to substantially form an osmotic passageway for the release of the active agent, such as ticagrelor in this present application, from the dosage form. A detailed description of the passageway can be found in U.S. Pat. Nos. 3,845,770, 3,916,899, 4,034,758, 4,063,064, 4,077,407, 4,088,864, 4,783,337, and 5,071,607, etc., the disclosures of which are hereby incorporate by reference.

In certain embodiments, the passageway is formed by laser drilling. In preferred embodiments, the dosage form contains one passageway, which is arranged on the drug layer side of each tablet in order provide the desired pharmacokinetic parameters of the formulation.

In preferred embodiments, the passageway is arranged to be within ±5 mm of the middle of each side of the tablet, the diameter of the passageway is between 0.20 to 2.00 mm, and the depth of passageway is between 0.10 to 2.50 mm.

According to some embodiments, the pharmaceutical composition comprises ticagrelor as the active drug agent, which can have an oral dosage form of 60-200 mg per tablet. The active drug agent ticagrelor is controlled released with the osmotic pump formulation, this design provides a controlled or sustained release formulation for ticagrelor for 15-24 hours that obtains peak plasma levels from 4 to 15 hours after administration under various conditions. The pharmaceutical composition disclosed herein can realize a controlled release of ticagrelor for up to about 24 hours and keep drug release rate variation less than 20% for 8-12 hours.

In the above embodiments, the additional drug agent could be configured to coated on the surface of the controlled membrane film tablet to release it immediately without affecting the timing of controlled release of the drug agent in the core tablet.

Furthermore, in the pharmaceutical composition, additional drug agent can be configured to have a dosage and a formulation that correspondingly matches with osmatic design of controlled release profile of the drug agent in the drug layer in the core tablet to thereby realize a quick starting effective dosage and maintain the effective dosage for 15-24 hours.

In the following, a total of eight examples (see Table 1) of the oral osmotic dosage delivery form of ticagrelor as described above are further provided, which are named "Ticagrelor ER Tablets" (i.e. ticagrelor extended release tablets) and are intended to describe and illustrate the various embodiments of the dosage form within the scope of the present disclosure. It shall be noted that these embodiments are given solely for the purpose of illustration, and are not intended to be construed as limitations of the present disclosure, as many variations thereof are possible without departing from the spirit and scope of the disclosure, which are also considered to be covered by the scope of the disclosure.

TABLE 1

Eight examples of oral dosage forms of ticagrelor and their compositions.

| | Example No. | | | | | | | |
|---|---|---|---|---|---|---|---|---|
| | 1 | 2 | 3 | 4 | 5 | 6 | 7 | 8 |
| Dosage of ticagrelor | 180 mg | 120 mg | 180 mg | 180 mg | 180 mg | 60 mg | 90 mg | 180 mg |
| First Drug Layer | | | | | | | | |
| 1. Ticagrelor | 180 | 120 | 120 | 135 | 150 | 60 | 90 | 90 |
| 2. PEO WSR N80 | 324 | 216 | 216 | 243 | 270 | 108 | 162 | 162 |
| 3. PVP K30 | 25 | 17 | 17 | 19 | 21 | 8.3 | 12.5 | 12.5 |
| 4. Stearic Acid | 2 | 1.3 | 1.3 | 1.5 | 1.7 | 0.7 | 1 | 1 |
| Push Layer | | | | | | | | |
| 1. PEO 303 | 178.5 | 119 | 119 | 134 | 149 | 59.5 | 89.3 | 89.3 |
| 2. Sodium Chloride | 75 | 50 | 50 | 56 | 63 | 25 | 37.5 | 37.5 |
| 3. PVP K30 | 15 | 10 | 10 | 11 | 12.5 | 5 | 7.5 | 7.5 |
| 4. Iron Oxide Red | 1 | 0.7 | 0.7 | 0.75 | 0.83 | 0.33 | 0.5 | 0.5 |
| 5. Stearic Acid | 1 | 0.7 | 0.7 | 0.75 | 0.83 | 0.33 | 0.5 | 0.5 |
| Semi-permeable Membrane | | | | | | | | |
| 1. Cellulose Acetate 398-10 | 72 | 48 | 48 | 54 | 60 | 33 | 40 | 40 |
| 2. PEG 6000 | 8 | 5 | 5 | 6 | 6.7 | 4 | 4.4 | 4.4 |
| Second Drug Layer | | | | | | | | |
| 1. Ticagrelor | 0 | 0 | 60 | 45 | 30 | 0 | 0 | 90 |
| 2. HPC | 0 | 0 | 20 | 20 | 20 | 0 | 0 | 0 |
| 3. PVA | 0 | 0 | 0 | 0 | 0 | 0 | 0 | 25 |
| 4. Titanium Dioxide | 0 | 0 | 10 | 10 | 10 | 0 | 0 | 15 |
| 5. Lactose Monohydrate | 0 | 0 | 10 | 10 | 10 | 0 | 0 | 0 |
| 6. PEG | 0 | 0 | 5 | 5 | 5 | 0 | 0 | 0 |
| 7. Triacetin | 0 | 0 | 5 | 5 | 5 | 0 | 0 | 10 |
| 8. Talc | 0 | 0 | 0 | 0 | 0 | 0 | 0 | 2 |
| Cosmetic Coating Layer | | | | | | | | |
| 1. HPMC | 25 | 25 | 25 | 25 | 25 | 20 | 20 | 25 |
| 2. PEG | 5 | 5 | 5 | 5 | 5 | 4 | 5 | 5 |

The following are noted for Table 1 regarding the preparation for each layer.

In the first drug layer, items 1 through 3 (i.e. "Ticagrelor", "PEO WSR N80", and "PVP K30", respectively, in the table) are blended in a planetary or a high shear mixer for approximately 15 minutes. This mixture is then wet granulated using purified water, USP to obtain a suitable consistency. The granulates obtained thereby are then passed through a mill and mesh screen to obtain suitable granules. The granules are next dried in a tray or a fluid bed drier. The dried granules are blended with item 4 (i.e. "Stearic Acid") for 5 minutes.

In the push layer: items 1 through 4 (i.e. "PEO 303", "Sodium Chloride", "PVP K30", and "Iron Oxide Red", respectively, in the table) are blended in a planetary or a high shear mixer for 15 minutes. This mixture is then wet granulated using purified water, USP to obtain a suitable consistency. The granulates are then passed through a mill and mesh screen to obtain suitable granules. The granules are next dried in a tray or a fluid bed drier. The dried granules are blended with item 5 (i.e. "Stearic Acid") for 5 minutes.

The drug layer granules and the push layer granules are then passed through a bilayer rotary tablet press to obtain the bilayer tablet cores of suitable strength.

In the semi-permeable membrane, item 1 (i.e. "Cellulose Acetate 398-10") is dissolved in 100% acetone, and item 2 (i.e. "PEG 6000") is dissolved in purified water. These two solutions are mixed and then used to coat the bilayer tablet cores produced above via a pan coater. A delivery passageway is then provided by drilling a hole through the coating into the core using a mechanical or laser drilling device.

In the second drug layer, item 1 and item 2 ((i.e. "Ticagrelor" and "HPC") are dissolved into ethanol to make a first solution, and the other items such as item 4 (i.e. "Titanium Dioxide"), item 5 (i.e. "Lactose Monohydrate"), item 6 (i.e. PEG), and item 7 (i.e. "Triacetin") are dissolved in the purified water to make a second solution. Then the first solution and the second solution are mixed. This mixed solution is then used to coat the membrane coated tablets produced above via a pan coater.

Alternatively, the second drug layer can be prepared by a different method. Specifically, item 1 (i.e. "Ticagrelor") is dissolved into ethanol to make a third solution, and the other items such as item 3 (i.e. "PVA"), item 4 (i.e. "Titanium Dioxide"), item 7 (i.e. "Triacetin"), and item 8 (i.e. "Talc") are dissolved in the purified water to make a fourth solution. Then the third solution and the fourth solution are mixed. This mixed solution is then used to coat the membrane coated tablets produced above via a pan coater.

In the cosmetic coating layer, items 1 and 2 (i.e. "HPMC" and "PEG") are dissolved in purified water. The coated tablets then coated with this solution via a pan coater.

A dissolution test has been carried out to examine the dissolution profile of each of the above eight examples of the oral dosage form of ticagrelor. Briefly, the dissolution test is performed with USP Apparatus II, with a paddle speed 75 rpm, and in 900 mL 0.20% SDS in the purified water solution, and the released ticagrelor is measured with an UV spectrometer with wavelength 255 nm. The dissolution results for the eight examples are respectively shown in FIGS. 2-9 and summarized in Table 2.

TABLE 2

Ticagrelor ER Tablets Dissolution Result.

| Timepoint (hr) | Example No. | | | | | | | |
|---|---|---|---|---|---|---|---|---|
| | 1 | 2 | 3 | 4 | 5 | 6 | 7 | 8 |
| 1 | 0 | 0 | 33 | 25 | 17 | 0 | 0 | 50 |
| 2 | 1 | 0 | 33 | 26 | 18 | 1 | 1 | 51 |
| 4 | 7 | 5 | 37 | 30 | 23 | 6 | 7 | 54 |
| 6 | 20 | 18 | 47 | 40 | 33 | 19 | 20 | 60 |
| 8 | 32 | 31 | 55 | 49 | 43 | 32 | 32 | 66 |
| 10 | 43 | 42 | 63 | 57 | 53 | 42 | 43 | 72 |
| 12 | 54 | 53 | 69 | 66 | 62 | 53 | 54 | 77 |
| 16 | 74 | 74 | 83 | 81 | 78 | 74 | 75 | 88 |
| 20 | 92 | 92 | 95 | 94 | 93 | 92 | 92 | 96 |
| 24 | 103 | 102 | 101 | 102 | 101 | 102 | 101 | 101 |

Note:
each value in each cell of the table represents the percentage of released ticagrelor (i.e. Release %) that is determined by the dissolution test at each corresponding specific timepoint (hour).

It should be noted that these above embodiments and examples of the pharmaceutical composition comprising ticagrelor serve as illustrating examples only and shall not be interpreted as limitations of the scope.

All references cited in the present disclosure are incorporated by reference in their entirety. Although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

The invention claimed is:

1. A dosage delivery form adapted to deliver ticagrelor to a subject in need, comprising: a core, comprising a first drug layer and a push layer stacked over one another; and a semi-permeable membrane coating an outside of the core; wherein: the first drug layer comprises a suspending agent and ticagrelor, wherein the suspending agent is polyethylene oxide, the ticagrelor is preset in an amount sufficient to deliver an effective amount thereof over an intended delivery time of 24 hours; the push layer comprises a swelling agent and an osmogen agent, wherein the swelling agent is polyethylene oxide; and the semi-permeable membrane is provided with at least one passageway formed therethrough, wherein the at least one passageway faces the first drug layer, but does not face the push layer, of the core, and is configured to allow the ticagrelor in the first drug layer to release out of the core therethrough when the dosage delivery form is in an aqueous environment, wherein more than 90% of ticagrelor is released at approximately 20 hours after dissolution in water, wherein the variation of a release rate of the ticagrelor is less than approximately 20% in a time period between approximately 6 hours and approximately 20 hours after dissolution in water.

2. The dosage delivery form of claim 1, wherein less than 15% of the ticagrelor from the first drug layer is released at approximately 4 hours after dissolution in water.

3. The dosage delivery form of claim 2, wherein approximately 45-65% of the ticagrelor is released at approximately 12 hours after the dissolution in water.

4. The dosage delivery form of claim 2, wherein the amount of the ticagrelor in the first drug layer is from about 50 mg to about 200 mg.

5. The dosage delivery form of claim 1, further comprising a second drug layer on the outside of the semi-permeable membrane, wherein the second drug layer comprises the ticagrelor.

6. The dosage delivery form of claim 5, wherein more than 15% of the ticagrelor is released at approximately 1 hour.

7. The dosage delivery form of claim 6, wherein a sum of the amount of the ticagrelor in the first drug layer and an amount of the ticagrelor in the second drug layer is from about 50 mg to about 200 mg.

8. The dosage delivery form of claim 5, further comprising a cosmetic coating layer coating an outside of the second drug layer.

9. The dosage delivery form of claim 1, wherein a number of the at least one passageway is one.

10. The dosage delivery form of claim 1, wherein the swelling agent in the push layer comprises polyethylene oxide having an amount of about 40% to about 80% in the push layer by weight.

11. The dosage delivery form of claim 10, wherein the swelling agent comprises at least one of Polyethylene Oxide having a molecular weight of approximately 4,000,000 g/mol, 5,000,000 g/mol or 7,000,000 g/mol.

12. The dosage delivery form of claim 1, wherein the osmogen agent in the push layer comprises at least one soluble inorganic salt, each selected from a group consisting of magnesium chloride, magnesium sulfate, lithium chloride, sodium chloride, potassium chloride, lithium hydrogen phosphate, sodium hydrogen phosphate, potassium hydrogen phosphate, lithium hydrogen phosphate, sodium hydrogen phosphate, potassium dihydrogen phosphate, or soluble salt of organic acid such as sodium acetate, potassium acetate, magnesium succinate, sodium benzoate, sodium citrate, and sodium ascorbate.

13. The dosage delivery form of claim 12, wherein the osmogen agent in the push layer comprises sodium chloride having an amount of about 10% to about 40% in the push layer by weight.

14. The dosage delivery form of claim 1, wherein the osmogen agent in the push layer comprises at least one non-ionic organic compound, each selected from a group consisting of arabinose, ribose, xylose, glucose, fructose, mannose, galactose, sucrose, maltose, lactose, and raffinose.

15. The dosage delivery form of claim 1, wherein the semi-permeable membrane comprises at least one of cellulose acetate, cellulose diacetate, cellulose triacetate, polyurethane, polyamide, sulfonated polystyrene, cellulose acetate valerate, or cellulose acetate succinate.

16. The dosage delivery form of claim 15, wherein the semi-permeable membrane comprises cellulose acetate having an amount of about 80% to about 100% in the semi-permeable membrane wall by weight.

17. The dosage delivery form of claim 15, wherein the semi-permeable membrane further comprises at least one plasticizing agent having a relative amount of approximately 0.1-40% of the semi-permeable membrane by weight.

18. The dosage delivery form of claim 17, wherein each of the at least one plasticizing agent is a polyalkylene glycol (PAG) or a polyethylene glycol (PEG) having a molecular weight of 300-8000.

19. The dosage delivery form of claim 18, wherein the at least one plasticizing agent comprises a polyethylene glycol (PEG), selected from PEG 6000 or PEG 8000.

* * * * *